United States Patent [19]

Rohlicek et al.

[11] Patent Number: 4,535,784
[45] Date of Patent: Aug. 20, 1985

[54] APPARATUS FOR STIMULATING ACUPUNCTURE POINTS BY LIGHT RADIATION

[75] Inventors: Vojtech Rohlicek; Jaroslav Hruby; Dusan Nohavica; Jan Hrdlicka; Vlastimil Vykouk; Frantisek Kubec, all of Prague, Czechoslovakia

[73] Assignee: Ceskoslovenska akademie ved, Prague, Czechoslovakia

[21] Appl. No.: 676,220

[22] Filed: Nov. 29, 1984

Related U.S. Application Data

[63] Continuation of Ser. No. 431,121, Sep. 30, 1982, abandoned.

[30] Foreign Application Priority Data

Oct. 9, 1981 [CS] Czechoslovakia ............ 7420-81
Oct. 13, 1981 [CS] Czechoslovakia ............ 7477-81
Apr. 22, 1982 [CS] Czechoslovakia ............ 2889-82
May 24, 1982 [CS] Czechoslovakia ............ 3816-82

[51] Int. Cl.³ .................................. A61H 39/00
[52] U.S. Cl. ........................... 128/735; 128/395; 128/907

[58] Field of Search .......... 128/395.8, 735, 419 R, 128/907; 219/121 L, 121 LM

[56] References Cited

U.S. PATENT DOCUMENTS 4,112,923 9/1978 Tomelek ....................... 128/735
4,232,678 11/1980 Skovajsa ....................... 128/395

FOREIGN PATENT DOCUMENTS 0058105 8/1982 France ........................... 128/907

Primary Examiner—Lee S. Cohen
Assistant Examiner—Steven Faln

[57] ABSTRACT

Apparatus for stimulating acupuncture points by light radiation in the visible light range or in the infrared range for medical purposes. An advantage of the apparatus of the invention resides in utilizing a very economical source of stimulating radiation, the radiation of which may be easily modulated and accurately focused, which considerably increases the efficiency of stimulation. An electrically conductive contact for locating acupuncture points, mounted directly in or on a transparent cover of a luminescent chip of a light emitting diode makes the locating of acupuncture points easy and accurate.

3 Claims, 8 Drawing Figures

APPARATUS FOR STIMULATING ACUPUNCTURE POINTS BY LIGHT RADIATION

This application is a continuation of application No. 431,121, filed Sept. 30, 1982 now abandoned.

FIELD OF THE INVENTION

This invention relates to an apparatus for stimulating acupuncture points by light radiation for medical purposes.

BACKGROUND OF THE INVENTION

When applying reflex therapeutics, various active points on a human body are stimulated, which are said to be acupuncture points. The stimulation of these acupuncture points may be carried out by applying needles, electric current, pressure, ultra-sound, heat or light.

There are hitherto known devices for the stimulation of these points by means of sources of coherent light—lasers, whether the are gas lasers or semi-conductor lasers.

A drawback of this solution resides especially in its high costs. The coherence of radiation is not necessary for the stimulation of acupuncture points.

There is also known the stimulation of acupuncture points by means of an incandescent lamp the light from which is focused on the surface of the skin corresponding to the effective surface of an acupuncture points.

A drawback of this solution resides in the considerable heating of the acupuncture point by the source of non-monochromatic light, so that in this case it does not produce a proper photostimulation, but represents a combination of a light stimulation with a heat stimulation which may cause pain.

There is also known the localization of acupuncture points by measuring their electrical impedance, which is considerably lower than the impedance of adjacent areas of the skin.

To locate acupuncture points, one usually applies a finding or locating metal electrode which is connected to an effective evaluating means, usually in the form of an impedance measuring instrument.

A drawback of this solution resides in the fact that it is necessary at first to determine the acupuncture point by means of a finding or locating electrode, then to mark the point, and finally, by means of another applicator provided with a source of light, to stimulate the thus found acupuncture point.

There is also known a device which employs a laser light as a stimulation source. Radiation is sent to the application spot through a flexible light guide cable, which passes into an electrode for the locating of finding of an acupuncture point.

A drawback of this solution resides in the considerable losses of the light output in the spot of the inlet of the radiation into the light guide cable.

SUMMARY OF THE INVENTION

The primary object of the apparatus of the invention for stimulating acupuncture points by light radiation, both visible and infrared, resides in the fact that the source of radiation is a light emitting diode. The light emitting diode may be advantageously provided with an electrode for contact with the skin connected to evaluating means for the location of acupuncture points. The electrode for contact with the skin may be advantageously connected to the evaluating means through one of the terminals or outlets of the light emitting diode.

The evaluating means may comprise a reference electrode and an impedance indicator provided with two input terminals, one of which is connected to the reference electrode and the other of which is connected to the electrode for contact with the skin.

An advantage of the apparatus for stimulating acupuncture points by light radiation according to the invention resides in the fact it utilizes a very economical source of stimulating radiation, viz. a light emitting diode, the radiation of which in the visible range, or in the infrared range, is nearly monochromatic; it may be well focused and easily modulated, which increases its stimulation efficiency. The light emitting diode may be easily situated directly in an applicator, so that it radiates acupuncture points directly and with a minimum of light losses. The electrode for contact with the skin may be mounted directly on a transparent cover of a luminescent chip, and in this way a high accuracy of localization of an acupuncture point may be achieved, and the stimulation of the acupuncture point may be carried out after its location without displacing the applicator upon the skin.

The apparatus is of small dimensions, and production costs and costs of operation are low; the apparatus may be fed from an electro-chemical source, and it makes it possible to carry out a painless and effective stimulation of accurately located acupuncture points.

In order that the invention may be clearly understood and readily carried into effect, preferred embodiments thereof are, by way of example, hereinafter more fully described and illustrated in the accompanying drawings, in which:

DESCRIPTION OF THE PREFERRED EMBODIMENTS

Figure 1:
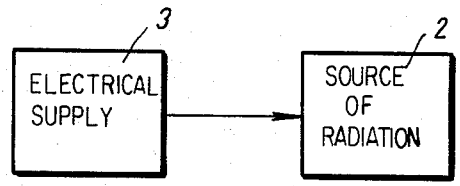
FIG. 1 is a block diagram of the apparatus.

FIG. 1 is a block diagram of the apparatus, such figure showing a source 2 of radiation connected to an electrical supply 3.

Figure 2:
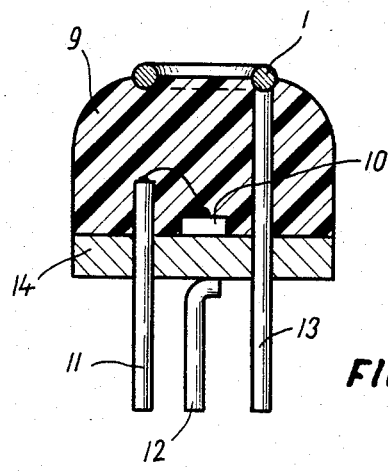
FIGS. 2-6, incl., respectively illustrate five examples of embodiments of a luminescent diode provided with an electrode for contact with the skin.

In FIG. 2 there is shown in section a first embodiment of acupuncture point locator in accordance with the invention, such device having a light emitting diode with an electrode for contact with the skin. A luminescent chip 10, connected to an outlet or terminal 11 and protected by a transparent cover 9, is welded onto a metallic base 14 which is which is conductively connected to a terminal 12. In the transparent cover 9 there is arranged an electrode 1 protruding out of the transparent cover 9 for contact with the skin. The electrode 1 for contact with the skin is shaped as a ring in this embodiment, and it is connected with a separate terminal 13 passing through the base 14.

It is to be understood that the terminals or outlets 11 and 13 are insulated from the base 14 and from each other.

Figure 3:
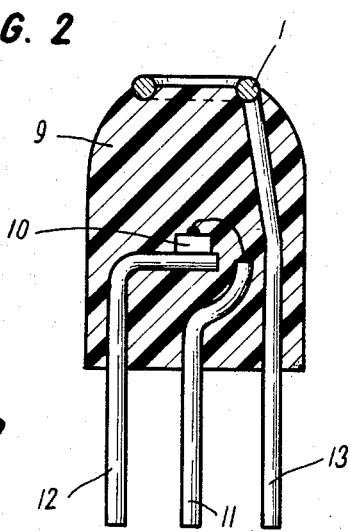

FIG. 3 illustrates a second embodiment of a light emitting diode with an electrode 1 for contact with the skin. Electrode 1 is connected to a terminal 13. The transparent cover 9, which as shown is made of plastic material, as is the cover in the embodiment of FIG. 2, is molded and itself, in this embodiment, functions as a base. The luminescent chip 10 is welded directly onto the terminal 12 and is connected to the terminal 11, in a known manner as shown.

Figure 4:
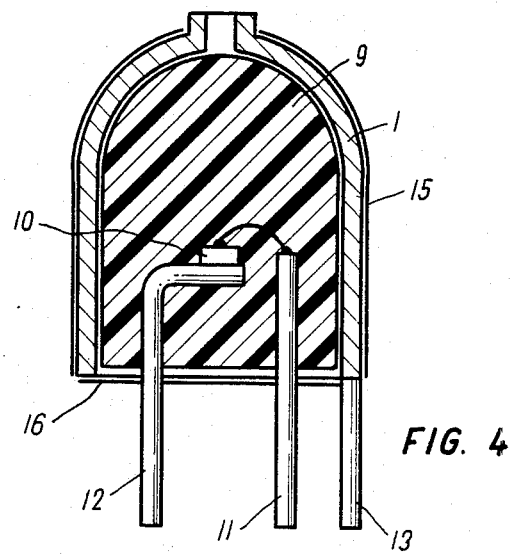

FIG. 4 showns in section a light emitting diode of an embodiment somewhat similar to that of FIG. 3, but with the difference that the electrode 1 for contact with the skin is connected to a separate terminal 13 which protrudes outwardly from the transparent cover 9. A part of the electrode 1 for contact with the skin is provided with an electrical insulating layer 15. The lower part of the transparent cover 9 is provided with a reflecting surface 16.

Figure 5:
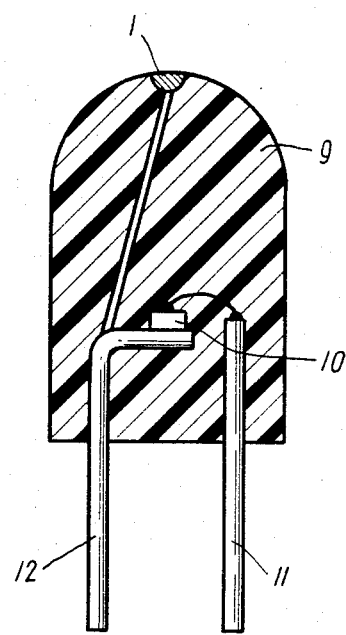

In FIG. 5 there is shown a still further embodiment of a light emitting diode, in such embodiment the electrode 1 for contact with the skin is not provided with a separate terminal, but is connected directly to the terminal 12 of the luminescent chip 10.

Figure 6:
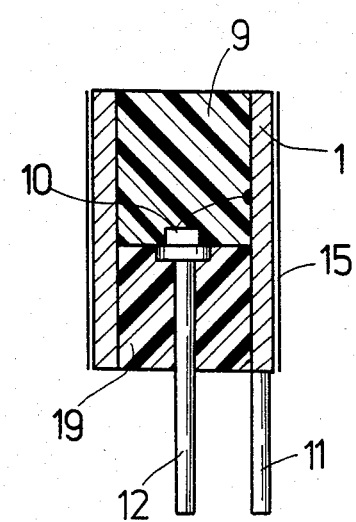

In FIG. 6 there is shown in section another embodiment of a light emitting diode with an electrode 1 for contact with the skin. The electrode 1 in this embodiment is shaped as a tube connected to the terminal 11 and electrically insulating plastic member 19 being telescoped within the lower end of the tubular member 1. Part 19 carries the terminal 12, upon the upper end of which there is mounted the luminescent chip 10 which is connected to the electrode 1 for contact with the skin. The chip 10 is protected by a transparent cover 9 made of plastic material. The circumferential surface of the electrode 1 is provided with a layer of electrically insulating material 15.

Figure 7:
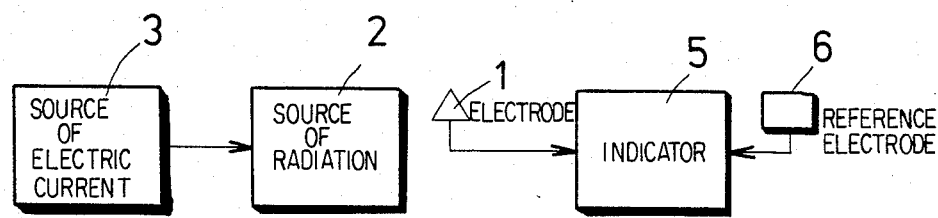
FIG. 7 is a block diagram of an apparatus with a locator of acupuncture points.

FIG. 7 is a block diagram of the apparatus according to the invention. A source 2 of radiation is connected to a source 3 of electric current. The electrode 1 for contact with the skin is connected to one of the terminals and indicator 5 for detecting variations in the impedance of the skin, a reference electrode 6 being connected to the other terminal of the indicator 5.

Figure 8:
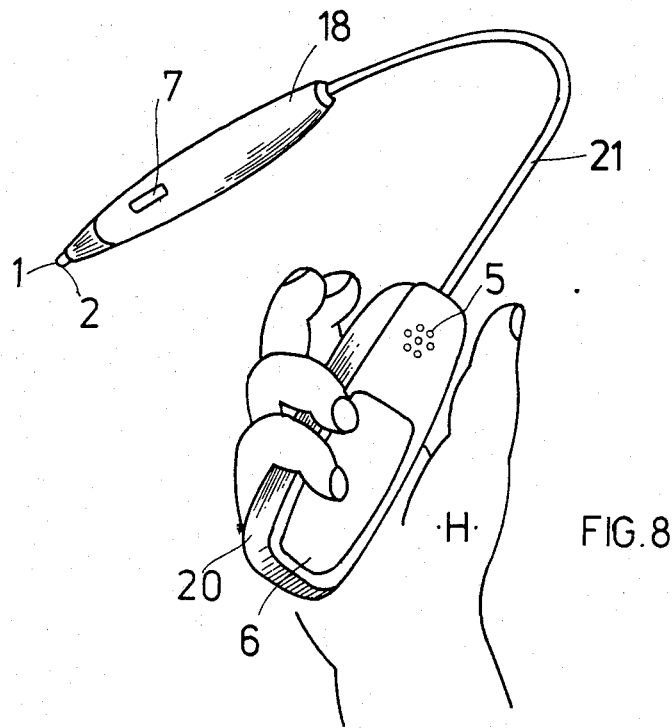
FIG. 8 is a view in perspective of a preferred operating embodiment of the apparatus in accordance with the invention.

FIG. 8 shows in perspective an operating example of the apparatus according to the invention. Such apparatus has a housing 20 with a reference electrode 6 and an indicator 5 for indicating impedance variations. The housing 20 is held in a hand H of a patient and is connected by means of a lead 21 to an applicator 18 comprising a source 2 of radiation and an electrode 1 for contact with the skin.

The source 2 of radiation is represented by a luminescent chip 10 of a light emitting diode, which gives a sufficient output of nearly monochromatic radiation of a suitable wavelength in the area of visible light or in the area of infrared radiation for stimulating acupuncture points. The source 2 of radiation is connected to the source of electric current 3 (FIG. 7) which suitably modulates the radiation, whereby to increase the efficiency of acupuncture points.

The electrode 1, for contact with the skin of a living creature, and which is provided with light from a light emitting diode, serves as a locating electrode for an accurate locating of acupuncture points on a human body. The reference electrode 6 is provided with an effective surface which is much larger than that of the locating electrode, and is usually held in the hand of the patient. Advantageously, it is arranged directly on the housing 20 of the apparatus, as shown in FIG. 8.

The electrode 1 for contact with the skin is connected by means of a separate oulet 13 (FIGS. 2, 3 and 4), or advantageously directly by means of one of the outlets 11 and 12 of the luminescent chip 10, to the electrical input of the indicator 5 of skin impedance variations, to which the reference electrode 6 is connected as well. The indicator 5 of skin impedance changes evaluates the impedance of a patient's skin in the spot under the electrode 1 for contact with the skin. It may be carried out e.g. by a variation of the intensity of sound produced by a sound producing device, or by the deflection of a pointer of a measuring instrument. As indicated above, the impedance of the skin, at the spot of an acupuncture point, is different from that of the surrounding area of the skin.

For an accurate location of an acupuncture point to be achieved, the effective surface of the electrode 1 must be small and it must be placed as near as possible to the point onto which the radiation is concentrated. Of course, this radiation must not be considerably screened by the electrode 1. The embodiments of the device of the invention shown in FIGS. 2-7, incl., are suitable for this purpose.

Dimensions of the effective surface of the electrode 1 for contact with the skin must not vary in dependence upon pressure exerted by the applicator 10 upon the skin. This is why, in examples of the light emitting diodes shown in FIGS. 4 and 6, a part of the surface of the electrode 1 is provided with an electrically insulating layer 15.

The source 2 of radiation for the electrode 1 is situated directly in the applicator 18, which makes it possible at first to locate the acupuncture point and then, immediately and without any displacement of the applicator 18, to stimulate such located acupuncture point by visible or infrared light.

The apparatus according to the invention may be advantageously applied for a painless reflex therapeutic treatment in hospitals, in ambulatory treatments, and even of treatments of a patient in the home.

Although the invention is described and illustrated with reference to a plurality of embodiments thereof, it is to be expessly understood that it is in no way limited to the disclosure of such preferred embodiments but is capable of numerous modification within the scope of the appended claims.

We claim:

1. An apparatus for stimulating acupuncture points on the skin of a living subject by light radiation and for detecting acupuncture points on the skin of a living subject by evaluating variations in skin impedance, comprising a light emitting diode and a surface electrode, said surface electrode being mounted on the surface of the light emitting diode for contact with the skin of the subject, a source of electric current for feeding the light emitting diode, circuit means for electrically connecting the light emitting diode with the source of electric current, and indicator means for evaluating variations in the impedance of skin of the subject at the location engaged by the suface electrode.

2. An apparatus as in claim 1 wherein the light emitting diode is provided with a plurality of terminals, and wherein the electrode is connected to the indicator means through one of the terminals of the light emitting diode.

3. An apparatus as in claim 1 wherein the indicator means comprises a reference electrode and a skin impedance indicator provided with two input terminals, one of the input terminals of the impedance indicator being connected to the reference electrode, and the other input terminal of said impedance indicator being connected to the surface electrode for contact with the skin of the subject.

* * * * *